(12) United States Patent
Harhen et al.

(10) Patent No.: US 8,070,685 B2
(45) Date of Patent: Dec. 6, 2011

(54) CONNECTORIZED PROBE FOR TRANSESOPHAGEAL ECHOCARDIOGRAPHY

(75) Inventors: Edward Paul Harhen, Duxbury, MA (US); Matthew Maher, Worchester, MA (US)

(73) Assignee: Imacor Inc., Uniondale, NY (US)

( * ) Notice: Subject to any disclaimer, the term of this patent is extended or adjusted under 35 U.S.C. 154(b) by 1177 days.

(21) Appl. No.: 11/279,510

(22) Filed: Apr. 12, 2006

(65) Prior Publication Data
US 2006/0235304 A1    Oct. 19, 2006

Related U.S. Application Data

(60) Provisional application No. 60/671,808, filed on Apr. 15, 2005.

(51) Int. Cl.
*A61B 8/00* (2006.01)
*A61B 8/12* (2006.01)
*A61B 1/00* (2006.01)
*A61B 1/005* (2006.01)

(52) U.S. Cl. ........ 600/462; 600/146; 600/149; 600/153; 600/459; 600/461; 600/463; 600/464; 604/22; 604/95.01; 604/95.04; 604/528; 604/535; 606/14; 606/15; 606/16

(58) Field of Classification Search .............. 600/146, 600/149, 153, 459, 461–464; 604/22, 95.01, 604/95.04, 528, 535; 606/14–16
See application file for complete search history.

(56) References Cited

U.S. PATENT DOCUMENTS

| | | | | |
|---|---|---|---|---|
| 3,154,890 A | * | 11/1964 | Lemelson | 451/165 |
| 3,892,228 A | * | 7/1975 | Mitsui | 600/149 |
| 3,948,251 A | * | 4/1976 | Hosono | 600/144 |
| 4,149,419 A | * | 4/1979 | Connell et al. | 73/621 |
| 4,543,960 A | * | 10/1985 | Harui et al. | 600/462 |
| 4,750,475 A | * | 6/1988 | Yoshihashi | 600/153 |
| 4,951,677 A | * | 8/1990 | Crowley et al. | 600/463 |
| 5,085,221 A | * | 2/1992 | Ingebrigtsen et al. | 600/446 |
| 5,178,149 A | * | 1/1993 | Imburgia et al. | 600/463 |
| 5,178,150 A | * | 1/1993 | Silverstein et al. | 600/463 |
| 5,181,514 A | * | 1/1993 | Solomon et al. | 600/444 |
| 5,195,519 A | * | 3/1993 | Angelsen | 600/454 |

(Continued)

FOREIGN PATENT DOCUMENTS

EP        0 654 245 A1    5/1995

(Continued)

OTHER PUBLICATIONS

Web page showing the AcuNav Imaging Catheter, 2002.

(Continued)

*Primary Examiner* — Unsu Jung
(74) *Attorney, Agent, or Firm* — Proskauer

(57) ABSTRACT

A connectorized ultrasound probe includes a distal section that is configured for insertion into a patient's body and a proximal section configured to interface the distal section with an ultrasound system. The distal section is easily attachable and detachable from the proximal section using at least one set of connectors. When connected, a user-operated actuator located on the proximal section controls the bending of the distal section, and the ultrasound system sends driving signals to and receives return signals from the ultrasound transducer via the proximal section. This arrangement is particularly advantageous for long term monitoring, because the disconnectability of the proximal section makes it possible to leave the distal section in place in the patient for longer periods of time without undue discomfort.

24 Claims, 12 Drawing Sheets

U.S. PATENT DOCUMENTS

| | | | | |
|---|---|---|---|---|
| 5,273,535 | A * | 12/1993 | Edwards et al. | 604/95.01 |
| 5,325,860 | A * | 7/1994 | Seward et al. | 600/468 |
| 5,351,691 | A * | 10/1994 | Brommersma | 600/462 |
| 5,405,337 | A | 4/1995 | Maynard | |
| 5,487,386 | A | 1/1996 | Wakabayashi et al. | |
| 5,544,660 | A * | 8/1996 | Crowley | 600/466 |
| 5,606,974 | A * | 3/1997 | Castellano et al. | 600/462 |
| 5,634,466 | A | 6/1997 | Gruner | |
| 5,695,491 | A * | 12/1997 | Silverstein | 606/1 |
| 5,713,363 | A * | 2/1998 | Seward et al. | 600/437 |
| 5,792,059 | A * | 8/1998 | Furia et al. | 600/459 |
| 5,797,844 | A * | 8/1998 | Yoshioka et al. | 600/442 |
| 5,820,549 | A * | 10/1998 | Marian, Jr. | 600/437 |
| 5,840,031 | A * | 11/1998 | Crowley | 600/440 |
| 5,993,378 | A * | 11/1999 | Lemelson | 600/109 |
| 6,007,531 | A * | 12/1999 | Snoke et al. | 606/15 |
| 6,053,871 | A * | 4/2000 | Cockburn | 600/459 |
| 6,083,170 | A | 7/2000 | Ben-Haim | |
| 6,142,945 | A | 11/2000 | Sakamoto et al. | |
| 6,171,249 | B1 * | 1/2001 | Chin et al. | 600/461 |
| 6,464,645 | B1 * | 10/2002 | Park et al. | 600/462 |
| 6,485,425 | B2 * | 11/2002 | Seward et al. | 600/442 |
| 6,494,843 | B2 * | 12/2002 | Edwardsen et al. | 600/463 |
| 6,530,897 | B2 * | 3/2003 | Nardeo | 604/95.04 |
| 6,547,739 | B2 * | 4/2003 | Jordfald et al. | 600/462 |
| 6,587,709 | B2 * | 7/2003 | Solf et al. | 600/424 |
| 6,749,572 | B2 * | 6/2004 | Edwardsen et al. | 600/459 |
| 6,752,800 | B1 * | 6/2004 | Winston et al. | 604/528 |
| 6,776,758 | B2 * | 8/2004 | Peszynski et al. | 600/437 |
| 6,814,727 | B2 * | 11/2004 | Mansouri-Ruiz | 604/535 |
| 6,916,306 | B1 * | 7/2005 | Jenkins et al. | 604/95.04 |
| 7,074,189 | B1 * | 7/2006 | Montegrande | 600/462 |
| 7,144,371 | B2 * | 12/2006 | Edwardsen et al. | 600/459 |
| 7,270,634 | B2 * | 9/2007 | Scampini et al. | 600/447 |
| 7,488,288 | B2 * | 2/2009 | Tanaka et al. | 600/459 |
| 7,722,532 | B2 * | 5/2010 | Ikeda et al. | 600/146 |
| 2003/0004460 | A1 | 1/2003 | Bedell | |
| 2003/0028107 | A1 * | 2/2003 | Miller et al. | 600/437 |
| 2003/0229287 | A1 * | 12/2003 | Flesch et al. | 600/466 |
| 2004/0073118 | A1 * | 4/2004 | Peszynski et al. | 600/459 |
| 2006/0052664 | A1 * | 3/2006 | Julian et al. | 600/146 |
| 2007/0083193 | A1 * | 4/2007 | Werneth et al. | 606/41 |
| 2009/0118618 | A1 * | 5/2009 | Harhen | 600/459 |

FOREIGN PATENT DOCUMENTS

| | | |
|---|---|---|
| EP | 0940116 | 9/1999 |
| JP | 7-391 | 1/1995 |
| JP | 7-250836 | 10/1995 |
| JP | 10-201759 | 8/1998 |
| JP | 11-244290 | 9/1999 |
| JP | 2000-14626 | 1/2000 |
| JP | 2001-509714 | 7/2001 |
| JP | 2004-229979 | 8/2004 |
| WO | 98/33428 | 8/1998 |

OTHER PUBLICATIONS

Product literature for Siemens Medical's Acuson AcuNa 8F Ultrasound Catheter, May 2005.

Instructional Guide for Siemens Medical's Acuson AcuNav Diagnostic Ultrasound Catheter, 2003.

Notification of intention to grant in corresponding EP application 06 824 701.4.

Office Action in related application JP2008506707.

Patent Abstracts of Japan 200014626 dated Jan. 18, 2000.

Patent Abstracts of Japan 10-201759 dated Aug. 4, 1998.

Patent Abstracts of Japan 2004229979 dated Aug. 19, 2004.

* cited by examiner

CONNECTORIZED PROBE FOR TRANSESOPHAGEAL ECHOCARDIOGRAPHY

CROSS REFERENCE TO RELATED APPLICATIONS

This application claims the benefit of U.S. Provisional Patent Application 60/671,808, filed Apr. 15, 2005.

BACKGROUND

U.S. application Ser. No. 10/996,816, filed Nov. 24, 2004, which is incorporated herein by reference, describes a unique ultrasound probe, transducer, and associated algorithm. The probe disclosed in the '816 application is significantly narrower than prior art devices, and can be left in place for extended periods of time. The primary intended use of that probe is for monitoring of the heart using echocardiography. FIG. 1 is a schematic representation of that probe 100. The probe has a flexible shaft 112 affixed to the end of an endoscope style control handle 104, and the distal end 116 of the probe 100 contains the ultrasound transducer 118. To use the probe, the distal end 116 is manipulated into position in the esophagus, and a bending mechanism is then actuated using actuator 102, which causes the bending section 114 of the probe to bend. In the context of echocardiography, this bending action is used to position the ultrasound transducer 118 in the fundus of the stomach to obtain an image of the transgastric short axis view of the heart. The handle 104 is connected to a connector 42 on the ultrasound system 40 via a cable 106 that terminates at a connector 108.

In the setting of an intensive care unit (ICU), patients are often maintained in a quiescent state for both the well-being of the patient and to facilitate the monitoring of various physiological functions. Leaving the probe 100 in place for extended periods of time, however, can create difficulties in common situations when the patient must be moved. (Examples of such situations include moving the patient to clean him or her, to prevent pressure sores, or to perform routine procedures.) If the probe 100 is kept in the patient while the probe is hooked up to the ultrasound system 40, moving the patient could be extremely difficult.

One solution to this problem is to detach the probe 100 from the ultrasound system 40 by disconnecting the probe's connector 108 from the ultrasound system's connector 42 before the patient is moved, to leave those portions of the probe that remain outside the patient's body 102-108 resting on a tray or a hook. However, since the handle 104 and associated cable portions 106 of the transesophageal echo (TEE) probe that remain attached to the patient are relatively large and heavy, this solution is somewhat clumsy, and requires an extra degree of awareness from the attendants so as to not dislodge the device or cause other problems due to paying too much attention to the device.

SUMMARY

A connectorized ultrasound probe includes a distal section that is configured for insertion into a patient's body and a proximal section configured to interface the distal section with an ultrasound system. The distal section is easily attachable and detachable from the proximal section using at least one set of connectors. When connected, a user-operated actuator located on the proximal section controls the bending of the distal section via the connectors, and the ultrasound system sends driving signals to and receives return signals from the ultrasound transducer via the proximal section.

DETAILED DESCRIPTION OF THE PREFERRED EMBODIMENTS

The drawbacks associated with a large handle and cabling that remains connected to the patient while the probe is in the patient's esophagus can be avoided or minimized by using a connectorized probe, with a distal portion that remains installed in the patient, and a detachable handle portion that interfaces with the distal portion. The connector passes both mechanical and electrical signals between the two portions. Optionally, the distal portion may be disposable, in which case it is preferable to reduce the cost of the distal portion. Because it is not disposable, the cost of the handle portion is less critical.

Figure 1:
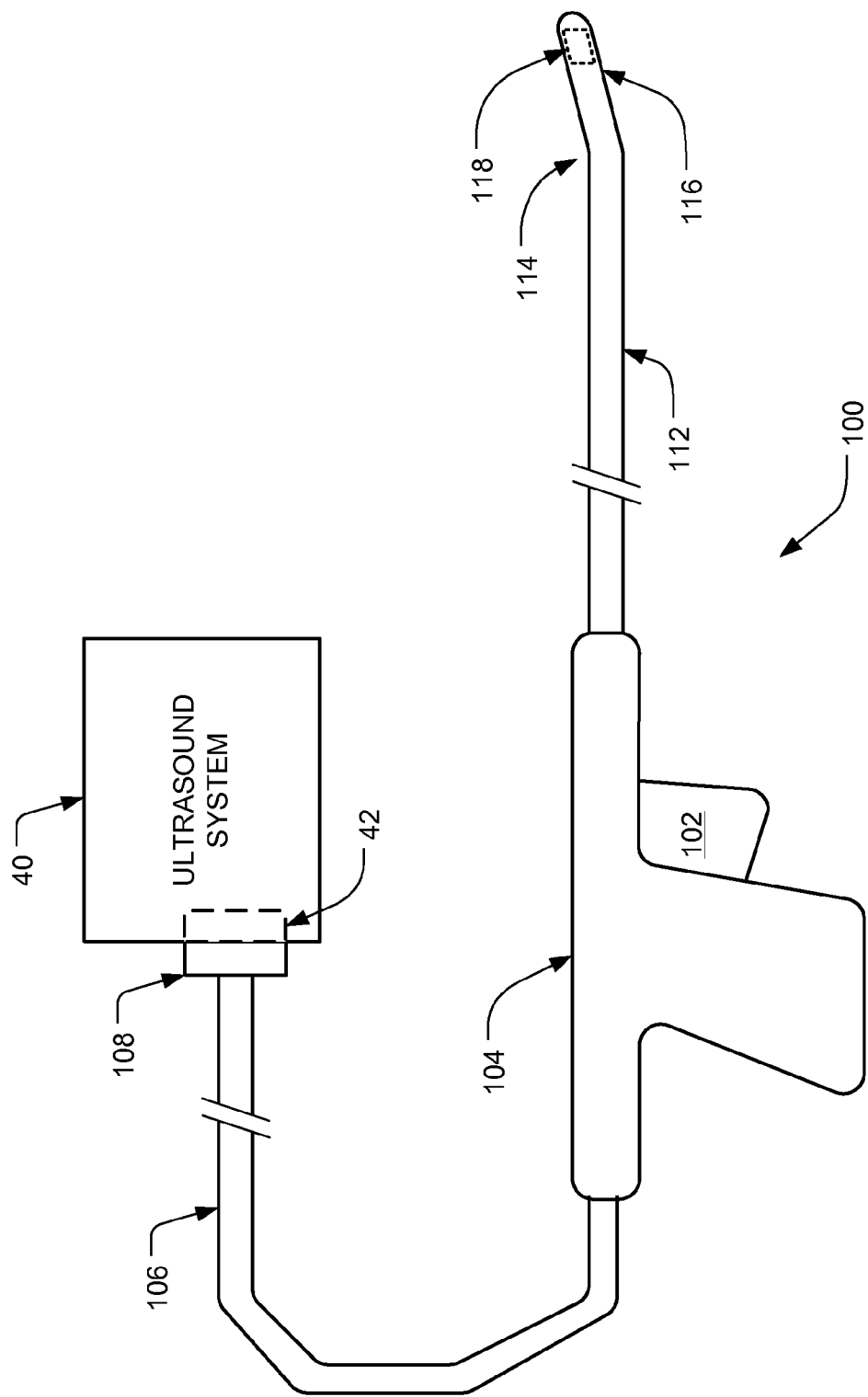
FIG. 1 is a schematic representation of the transesophageal echocardiography ultrasound probe disclosed in the '816 application.
Figure 2:
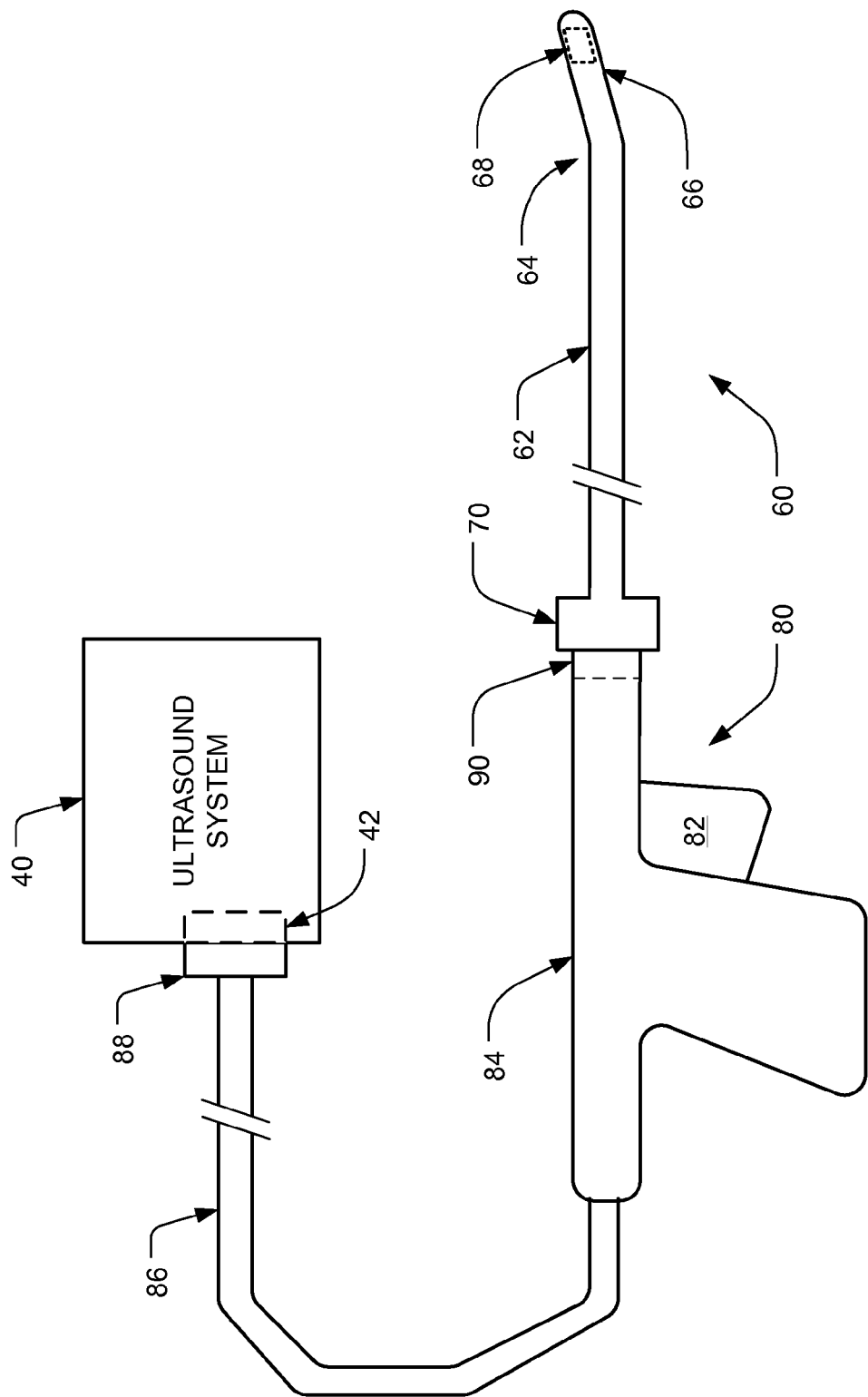
FIG. 2 is a schematic representation of a first embodiment of an improved ultrasound probe for transesophageal echocardiography in accordance with the present invention.

FIG. 2 is a schematic representation of an embodiment of the invention, with a probe that includes an actuator assembly 80 and a transducer assembly 60. The actuator assembly 80 includes a control handle 84 with an actuator 82. The handle 84 is connected to a connector 42 on the ultrasound system 40 via a cable 86 that terminates at a connector 88. The transducer assembly 60 has a flexible shaft 62 affixed to the end of a connector 70, and the distal end 66 of the probe contains the ultrasound transducer 68. To use the probe, the actuator assembly 80 and the transducer assembly 60 are connected together by mating the first connector 90 with the second connector 70. The distal end 68 is then manipulated into position in the esophagus. The transducer assembly 60 includes a bending mechanism that is actuatable by the actuator 82 when the actuator assembly 80 and the transducer assembly 60 are connected together. This causes the bending section 64 of the probe to bend to provide an end result that is similar to the bending achieved in the unitary probe described above in connection with FIG. 1.

Now, when it becomes necessary to move the patient, the transducer assembly 60 is disconnected from the actuator assembly 80 at the connectors 70, 90, so that the only parts that remain protruding from the patient will be the proximal end of the shaft 62 and the connector 70. Since those portions are relatively small and light compared to the handle 104 and cable 106 of the probe 100 depicted in FIG. 1, it becomes much easier to leave the distal end of the probe in the patient when the patient has to be moved or cared for.

Figure 3:
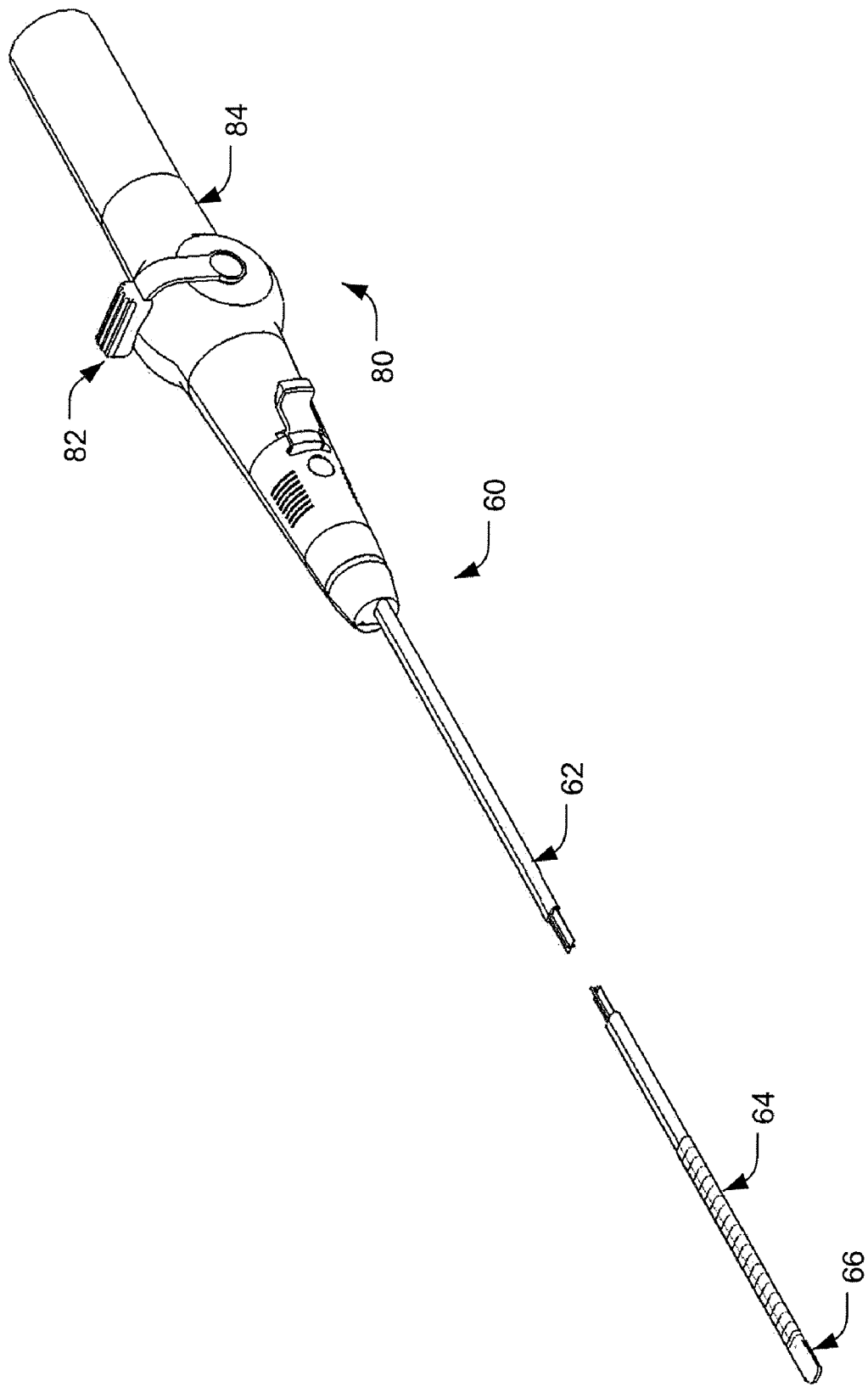
FIG. 3 is an isometric view of an implementation of the ultrasound probe of FIG. 2, with a transducer assembly connected to a matching actuator assembly.

FIG. 3 depicts a preferred implementation of the FIG. 2 embodiment, with the transducer assembly 60 mounted to the actuator assembly 80. The transducer assembly 60 include includes a flexible shaft 62 (shown with a break to denote its long length) that has a bending section 64. The shaft 62 is preferably less than 6 mm in diameter, and preferably on the order of 1 m in length for an adult version of the device. Those dimensions may be scaled down appropriately for pediatric and neonatal patients. The distal end 66 of the transducer assembly 60 houses the ultrasound transducer which is preferably transversely oriented with respect to the proximal distal axis. In alternative embodiments, other transducer configurations may be used in place of the transversely oriented transducer (e.g., a two-dimensional ultrasound transducer or a rotating multi-plane transducer). The actuator assembly 80 includes a handle 84 with a user-operated actuator 82 mounted on the handle. A cable 86 with a connector 88 at its proximal end (both shown in FIG. 2) extends from the proximal end of the handle 84. This connector 88 mates with a corresponding connector 42 on the ultrasound system 40 (all shown in FIG. 2).

Figure 4:
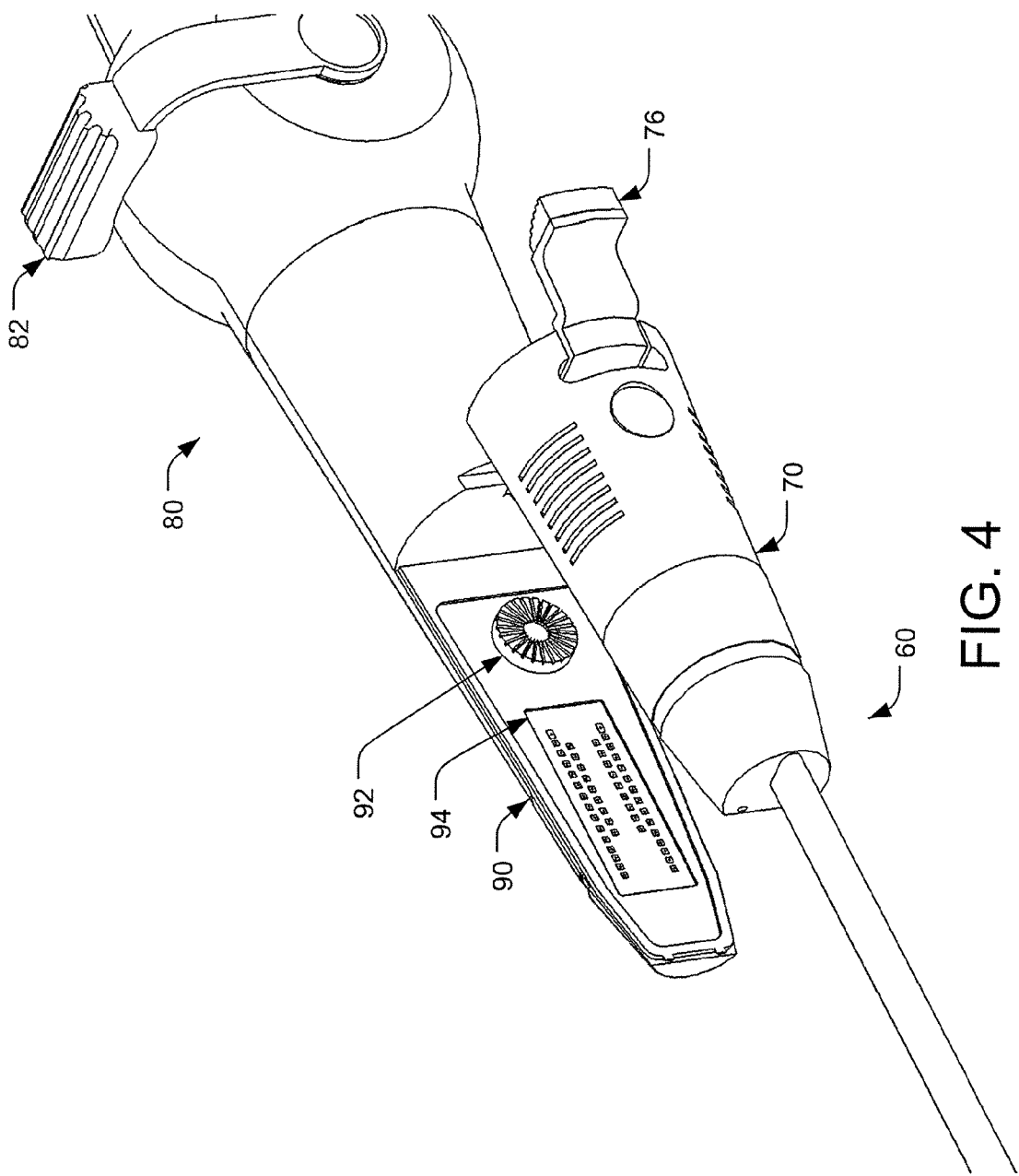
FIG. 4 is a first detailed view of the interface between the transducer assembly and the actuator assembly of the FIG. 3 embodiment.

FIG. 4 is an exploded detail view of the interface between the actuator assembly 80 and the transducer assembly 60. The actuator assembly 80 includes a first connector 90 that interfaces with the transducer assembly 60, and the transducer assembly 60 includes a second connector 70 that interfaces with the actuator assembly 80. The first connector 90 includes a first electrical interface 94, which is used to make electrical connect with a mating connector (not shown) on the second connector 70. In the illustrated embodiment, the first electrical interface 94 comprises a series of conductive pads, which are preferably gold plated. The pads may be flat or raised. Preferably, the first connector is constructed to be watertight so that the first connector can be immersed in a liquid sterilant (e.g., Cidex glutaraldehyde, peroxide sterilants, etc.), and using simple, stationary pads helps achieve the desired watertightness, which facilitates re-use of the actuator assembly 80 for multiple patients. When the second connector 70 is mated to the first connector 90, corresponding contacts on the second connector 70 line up with the contacts of the first electrical interface 94 so that electrical signals can pass between the actuator assembly 80 and the transducer assembly 60.

The ultrasound system 40 communicates with the ultrasound transducer 68 (both shown in FIG. 2) by sending and receiving appropriate signals into the actuator assembly 80 via the connector 42, the connector 88, and the cable 86 (all shown in FIG. 2). The signals that travel through the cable 86 are routed to the first electrical interface 94 on the first connector 90 e.g., by running appropriately shielded wires from the distal end of the cable 86 directly to the first electrical interface 94. Optionally, appropriate intervening circuitry (e.g., amplifiers, signal conditioners, etc.) may be interposed between the first electrical interface 94 and the cable 86. The remainder of the path to the transducer is described below in connection with the transducer assembly 60.

The first connector 90 also includes an output actuator 92 that is designed to mate with a corresponding member on the second connector 70 when the second connector 70 is connected to the first connector 90. The output actuator 92 is linked to the user-operated actuator 82 by an appropriate mechanism such that the output actuator moves in response to user actuation of the user-operated actuator 82. The link between the user-operated actuator 82 and the output actuator 92 may be implemented using any of a variety of conventional techniques, including but not limited to gears, pull wires, servo motors, stepper motors, hydraulics, as well as numerous other techniques that will be apparent to persons skilled in the relevant arts. The output actuator 92 and the user-operated actuator 82 are preferably also made using a watertight construction (e.g., using O rings or other sealing techniques) to facilitate liquid sterilization of the actuator assembly 80.

Figure 5:
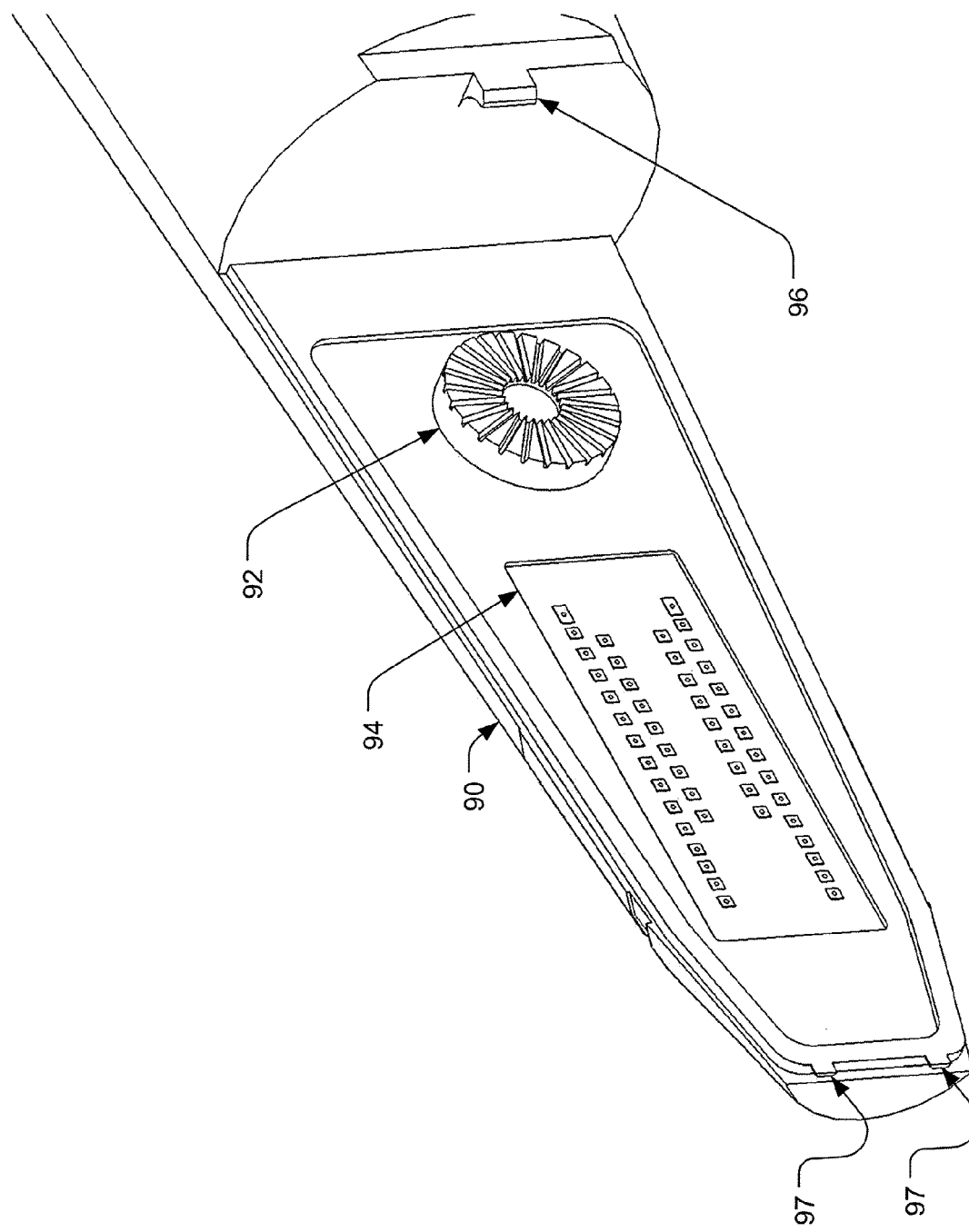
FIG. 5 is a detailed view of the interface portion of the actuator assembly of the FIG. 3 embodiment.

FIG. 5 shows the first connector 90 in even greater detail. As explained above, the output actuator 92 rotates in response to actuations of the user-operated actuator 82. The surface of the output actuator 92 is preferably made of a material that will have a high coefficient of friction when it is pressed against a corresponding member in the second connector 70. Examples of suitable materials for the output actuator include rubber, polyethylene, polystyrene, vinyl, etc. Optionally, a plurality of radial grooves may be cut into the surface of the output actuator 92 to help the output actuator 92 better "grab" the corresponding surface on the second connector 70.

As best seen in this view, the first connector 90 includes a number of mounting members for latching the first connector onto the second connector. Although the illustrated embodiment depict mounting members in the form of a pair of small tabs 97 at the distal end and a larger tab 96, persons skilled in relevant arts will recognize that any of a wide variety of conventional latching mechanism may be used.

Figure 6:
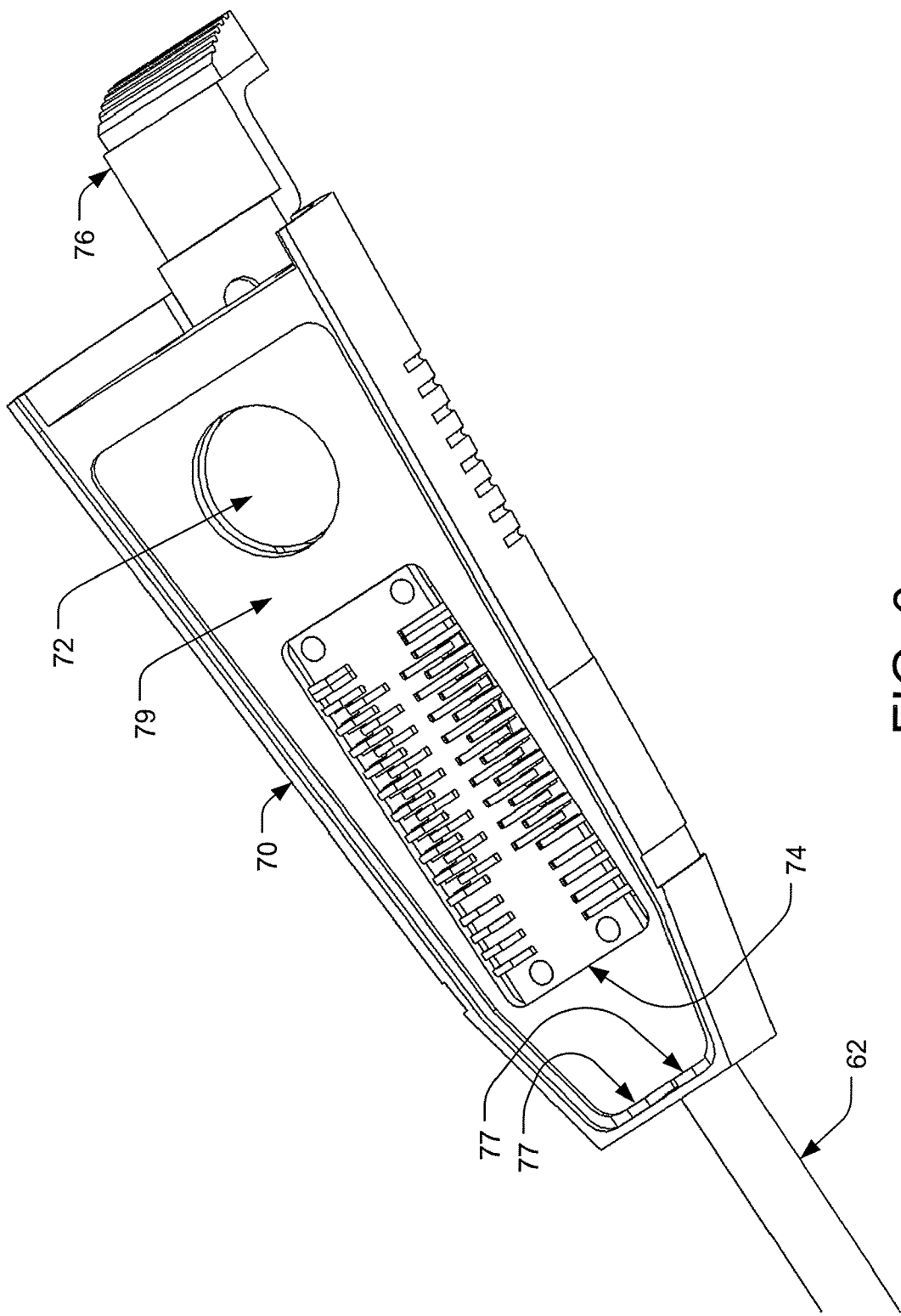
FIG. 6 is a detailed view of the interface portion of the transducer assembly of the FIG. 3 embodiment.

FIG. 6 is a front view of the second connector 70. The second connector 70 is configured to mate with the first connector 90. To do this, the second connector 70 contains a second electrical interface 74 that lines up the first electrical interface 94 of the first connector 90. In the illustrated embodiment, the second electrical interface 74 is made using a plurality of spring loaded fingers positioned so that, when the second connector 70 is connected to the first connector 90, the fingers of the second electrical interface 74 will line up with the pads of the first electrical interface 94 (shown in FIGS. 4, 5). The second connector 70 also contains a control actuator 72 that lines up the output actuator 92 of the first connector 90, so that the output actuator 92 can drive the control actuator 72. In the illustrated embodiment, the control actuator 72 is a rotating wheel that is designed to be driven by rotation of the output actuator 92. Of course, a wide variety of alternative arrangements for actuating alternative control actuators will be readily apparent to persons skilled in the relevant arts. Note that when the transducer assembly 60 is disposable and will be discarded after each use, it is not necessary to make the second connector 70 watertight.

To connect the first and second connectors, the second connector 70 is attached to the first connector 90 by aligning the notches 77 of the second connector 70 with tabs 97 of the first connector 90, then squeezing the proximal end of second connector 70 towards the first connector 90. The latching arm 76 on the second connector 70 is designed to snap into position on the first connector by interacting with tab 96 (shown in FIG. 5). When the first connector 70 is attached to the first connector 90 in this manner, the second electrical interface 74 of the second connector 70 makes electrical connect with the first electrical interface 94 of the first connector 90, so that electrical signals can travel back and forth between the first electrical interface 94 and the second electrical interface 74. In addition, the control actuator 72 makes mechanical connect with the output actuator 92 of the first connector 90, so that when the output actuator 92 is rotated in response to operation of the user operated actuator 82 (shown in FIG. 4) the control actuator 72 will be driven by the output actuator 92 and followed the rotation of the output actuator 92. A lid 79 protects the internal components of the second connector 70 from damage, and has cutouts to provide access to the second electrical interface 74 and the control actuator 72. Note that while FIGS. 4-9 depict first and second electrical interfaces 94, 74 using pads and fingers designed to contact the pads, numerous alternative electrical interfaces (e.g., pins and mating sockets) may be substituted therefore, as will be appreciated by persons skilled in the relevant arts.

Figure 7:
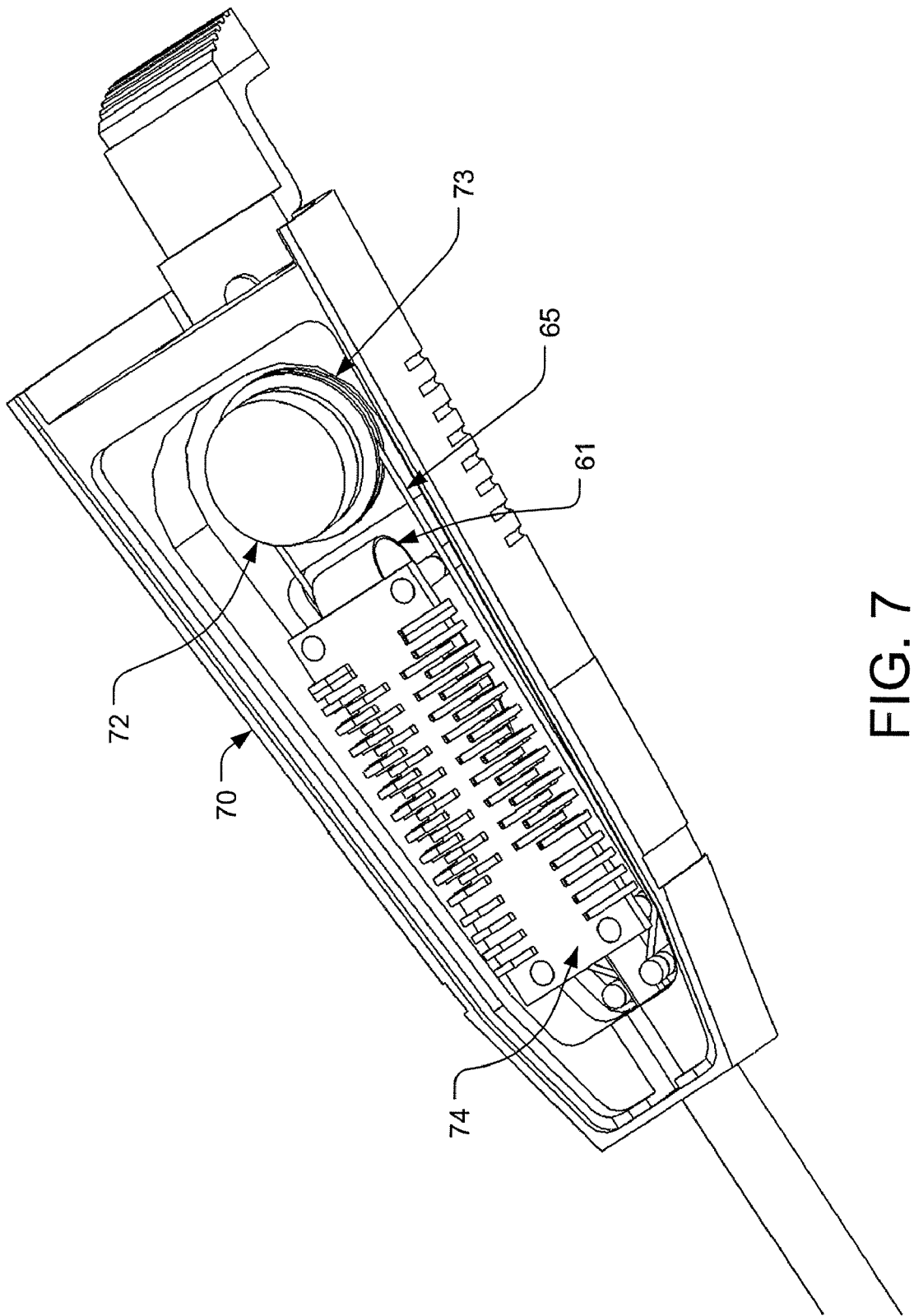
FIG. 7 shows the internal components of the transducer assembly of FIG. 6, with the lid removed.

FIG. 7 is another view of the second connector 70 shown in FIG. 6, with the lid 79 removed. This view reveals that the rotating control actuator 72 is attached to a pulley 73 that causes the pull wires 65 to move when the control actuator 72 is rotated. This view also shows a portion of the ribbon cable 61, which is the wiring that connects the second electrical interface 74 to the transducer 68 (shown in FIG. 2) at the distal end 66 of the transducer assembly 60. Preferably, a ground plane is provided on both sides of the ribbon cable. In less preferred embodiments one or both of those ground planes may be omitted, or wiring configurations other than ribbon cable may be used. Optionally, appropriate intervening circuitry (e.g., amplifiers, signal conditioners, etc.) may be interposed between the second electrical interface 74 and the transducer 68.

Figure 8:
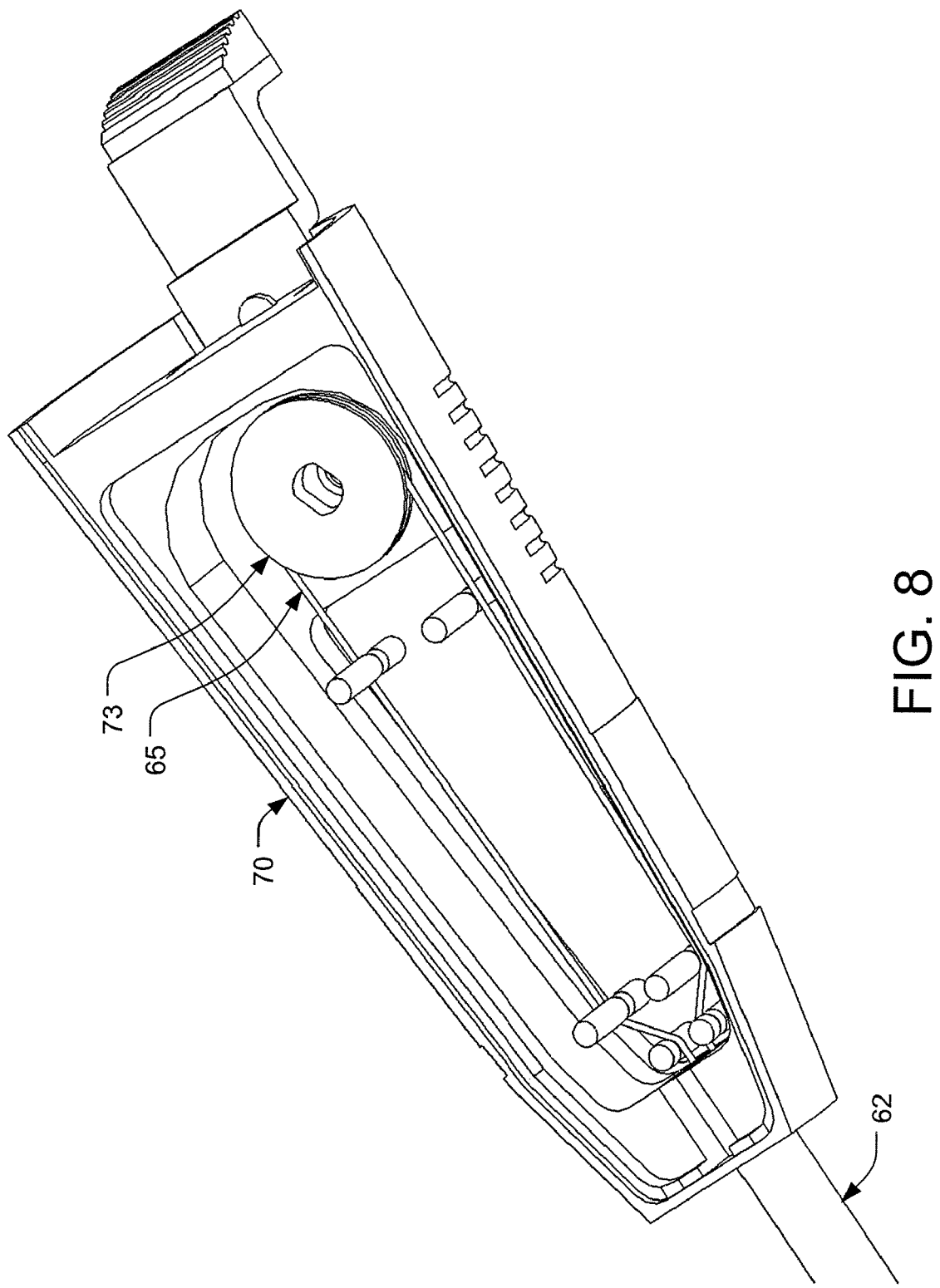
FIG. 8 shows the transducer assembly of FIG. 6, with certain components removed to make the lower components visible.

FIG. 8 shows yet another view of the second connector 70 of FIGS. 6 and 7, but with the lid 79, the second electrical interface 74, the wiring 61, the control actuator 72, and the pulley's axle all removed to show the lower components of the second connector 70. This view more clearly shows how the pulley 73 moves the pull wires 65, which extend out distally through the shaft 62. When the pull wires 65 move (in response to rotation of the pulley), the pull wires operate the bending section 64 (shown in FIG. 3) in any conventional manner. Since the pull wires 65 cause the bending section 64 to bend, and the pull wires 65 are moved by rotation of the pulley 73, and rotation of the pulley 73 occurs in response to rotation of the control actuator 72 (shown in FIGS. 6 and 7), the net result is that rotation of the control actuator 72 causes the bending section 64 to bend.

Figure 9:
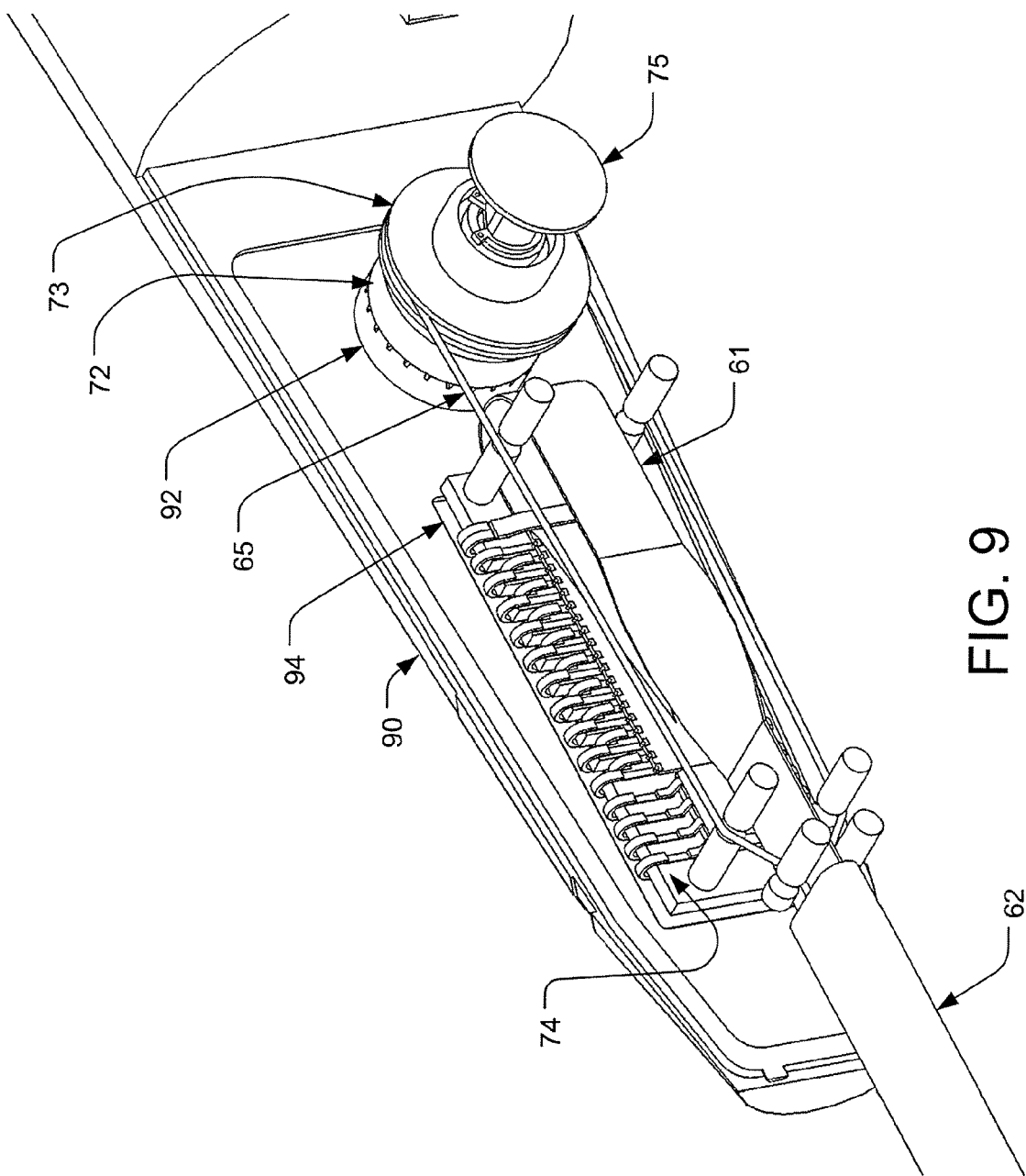
FIG. 9 shows the electrical and mechanical interactions between the transducer assembly and the actuator assembly when those two assemblies are mated together.

FIG. 9 shows the electrical and mechanical interactions between the first connector 90 and the second connector 70 when those connectors are mated together. This view depicts the mated set of connectors 90, 70 would look if the outside housing of the second connector 70 were invisible. The second electrical interface 74 is lined up with and urged against the first electrical interface 94, and the control actuator 72 on the second connector 70 is lined up with and urged against the output actuator 92 on the first connector 90. A pulley mount 75 permits the pulley 73 to rotate and urges the control actuator 72 against the output actuator 92 when the first connector 90 and second connector 70 are mated. The ribbon cable 61 that connects the second electrical interface 74 to the transducer 68 (shown in FIG. 2) at the distal end 66 of the transducer assembly 60 is also more clearly visible in this view.

When the second connector 70 is mated with the first connector 90, actuation of the user operated actuator 82 (shown in FIGS. 3 and 4) will cause the output actuator 92 to rotate. Since the control actuator 72 is being urged up against the output actuator 92, the control actuator 72 will follow the rotation of the output actuator 92. Rotation of the control actuator 72 turns the pulley 73 which operates the pull wires 65 that extend distally through the flexible shaft 62, and cause a bending mechanism (not shown) located in the bending section (shown in FIG. 3) to bend. Thus, when the second connector 70 is mated to the first connector 90, actuation of the user operated actuator 82 by the user will have the same net effect of actuations of the user operated actuator 102 of the unitary probe 100 depicted in FIG. 1. Note that while FIGS. 4-9 depict using rotating pads for the output actuator 92 and the control actuator 72 pads, numerous alternative mechanical interfaces (e.g., gears, a hexagonal shaft and a mating socket, etc.) may be substituted therefore, as will be appreciated by persons skilled in the relevant arts.

In addition, when the second connector 70 is mated with the first connector 90, the second electrical interface 74 makes contact with the first electrical connector 94. Since the first electrical connector 94 communicates with the ultrasound system 40 via cable 86 and connectors 88, 42 (all shown in FIG. 2), and Since the wiring 61 connects the second electrical interface 74 to the transducer 68 at the distal end 66 of the transducer assembly 60 (shown in FIGS. 2, 3) this arrangement permits the ultrasound system 40 to interface with the transducer 68 in the same way that the ultrasound system 40 communicates with the transducer 118 in the unitary probe 100 depicted in FIG. 1. Optionally, additional signals may be passed to and from the transducer assembly 60 via the first and second connectors 90, 70, e.g., to operate a thermistor located in the distal end of the transducer assembly 60 or to interface with a non-volatile memory device located in the transducer assembly 60 (used, e.g., to store data relating to the transducer assembly 60).

As best seen in FIGS. 4 and 9, the electrical and mechanical interface between the transducer assembly 60 and the actuator assembly 80 is sideways-facing (i.e., the mating surfaces of the first and second connectors 90, 70 face in a direction that is roughly perpendicular to the proximal-distal axis). This arrangement stands in contrast to the situation where one mating surface faces distally, and the other mating surface faces proximally (like the interface between the connectors 12, 22 in the FIG. 10 embodiment described below). Using a sideways-facing interface advantageously provides a large amount of "real estate" (i.e., area) for implementing the electrical and mechanical connections between the two assemblies. Moreover, despite the fact that a large amount of real estate is available for the interface, the overall diameter of the assemblies 60, 80 when connected can remain small (e.g., about 22 mm, measured at the proximal end of second connector 70 in the embodiment illustrated in FIGS. 3-9), and does not have to increase in proportion to the number of connections that are made between the first and second connectors 90, 70.

Figure 10:
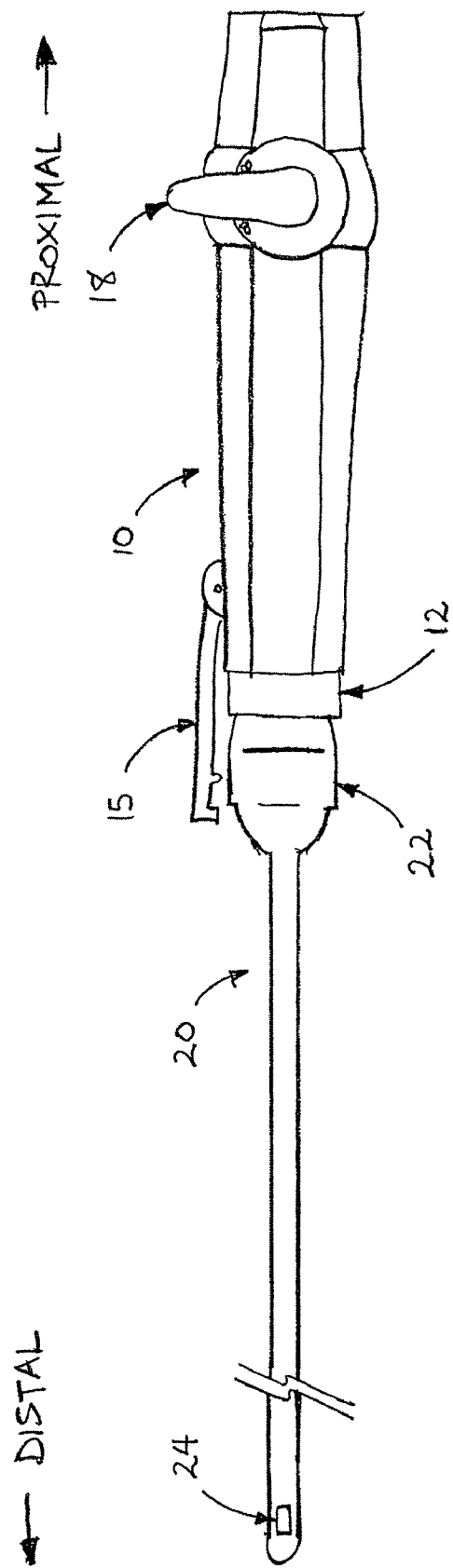
FIG. 10 is another embodiment of an improved ultrasound probe for transesophageal echocardiography in accordance with the present invention.
Figure 11:
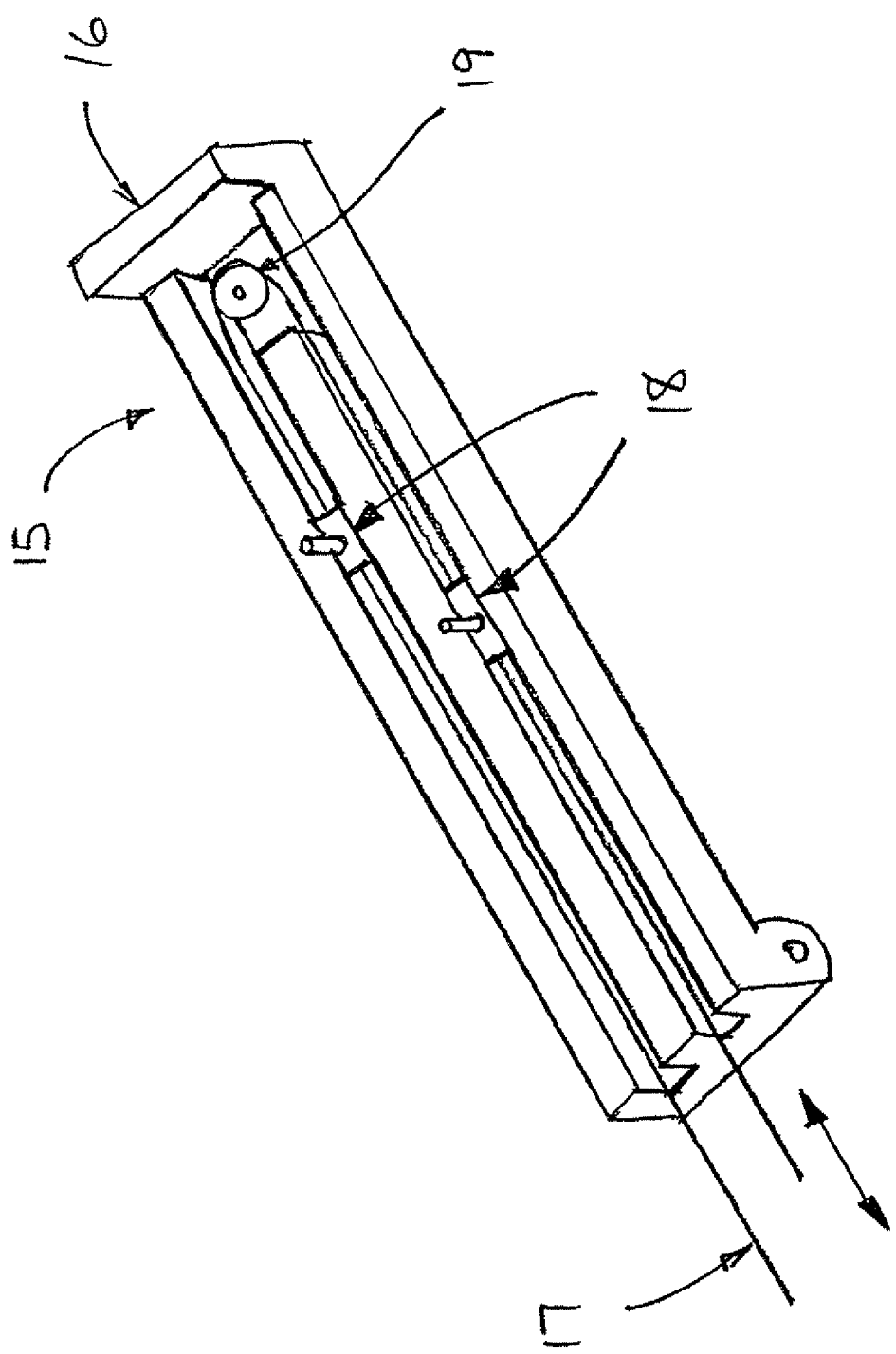
FIG. 11 is a detail of the mechanical connection on the actuator assembly side of the probe of FIG. 10.

FIG. 10 is another embodiment of the invention in which the insertion tube and acoustic block assembly (referred to above as the transducer assembly) are separable from the control handle (referred to above as the actuator assembly). In this embodiment, a durable handle 10 is connected to the transducer assembly 20. A connector 12 at the distal end of the handle 10 mates with a corresponding connector 22 at the proximal end of the transducer assembly 20. FIG. 11 shows a detail of the latching arm 15 of the handle portion 10, and FIG. 12 shows a detail of the connector portion 22 of the transducer assembly 20.

Figure 12:
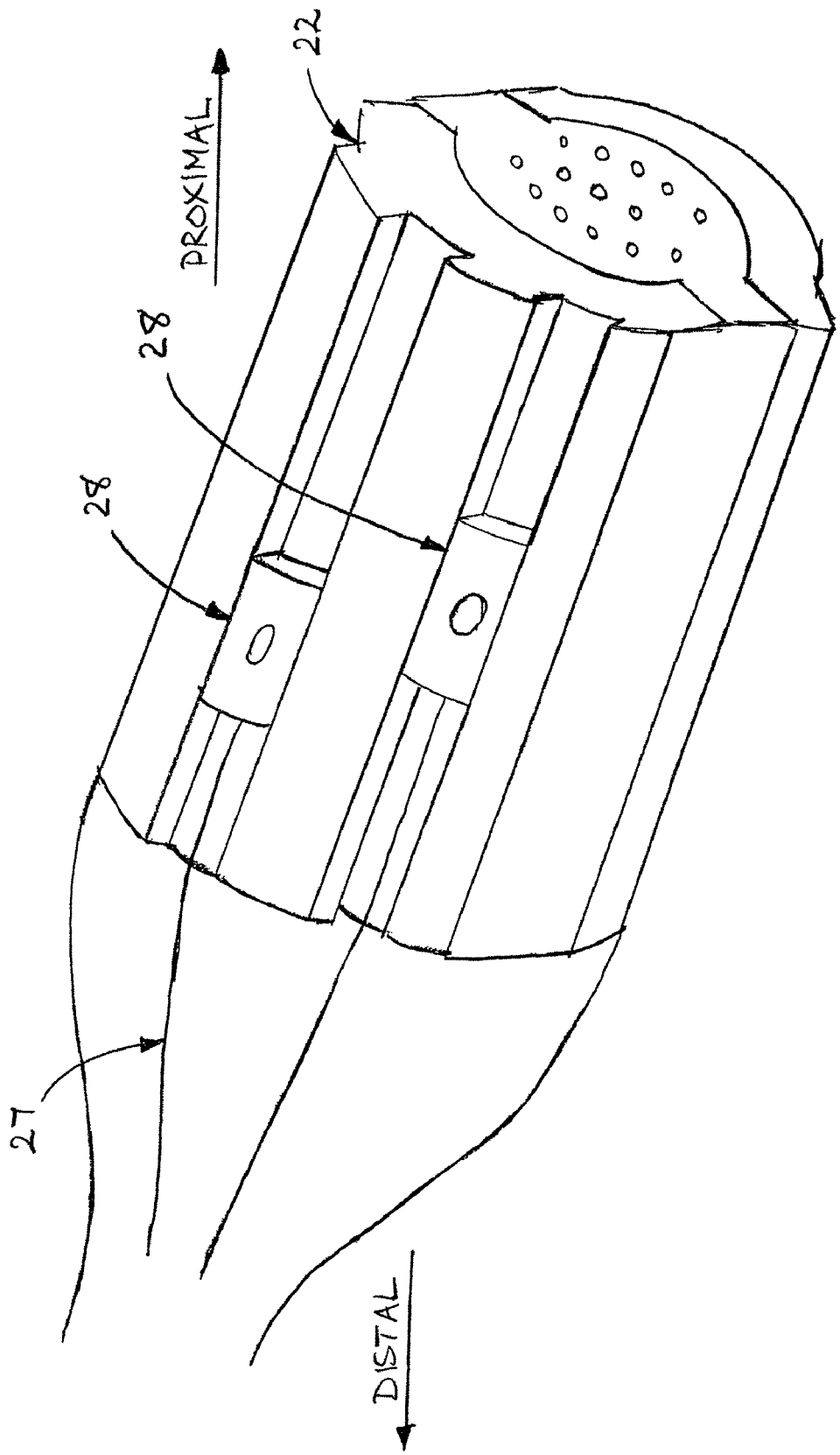
FIG. 12 is a detail of the mechanical connection on the transducer assembly side of the probe of FIG. 10.

Referring now to FIGS. 10-12, the connectors 12, 22 provide a detachable electrical interface to get all the necessary electrical signal to the distal end of the probe, and to receive return signals from the distal end of the probe. For example, the electrical connections may be used to pass signals used for generation of ultrasound at the ultrasound transducer 24, return of electrical signals from the transducer, ground and shielding planes, and any other electrical functions that are implemented at the distal end (e.g., connections to a non-volatile memory device may be integrated into the transducer assembly).

The connector 22 and the arm 15 also provide a detachable mechanical interface to actuate controllable portions at or near the distal end of the probe. An example of a desirable mechanical motion is flexing of the tip of the probe, which may be useful after the probe has been positioned in the fundus of the stomach. In the illustrated embodiment, the mechanical interface is implemented using pull wires that are connected to the distal end of the probe, where they initiate the desired motion (e.g., flexing of the probe tip). The mechanism that responds to the pull wires at the distal end of the probe may be implemented in any conventional manner. At the proximal end of the transducer assembly 20, the pull wires terminate in sliders 28 with a female hole.

To use the probe, the connector 22 is mated with the corresponding connector 12 of the handle, and the latching arm 15 is moved into position so that its pins 18 are mated into the sliders 28 of the transducer assembly 20. The latching arm may include a catch 16 to hold the transducer assembly 20 to the handle portion 10. The slides 18 are connected to each other via flexible cabling 17 which traverses a pulley 19 at the distal end of the latching arm 15. This configuration helps insure that articulation control cable stays taut within the handle and does not require the use of springs to take up slack.

The handle 10 includes a control surface 18 which may be implemented in any conventional way e.g., using pull wires. However, instead of having the pull wires go directly to the distal end of the probe, the pull wires the handle move the sliders 18 in the arm 15. Those sliders 18 in turn move the sliders 28, which move the pull wires 27 that run through the lumen of the transducer assembly 20 to generate the desired motion at the distal end of the probe. The result is a distal articulation mechanism that passes through a connector.

One suitable way to implement the electrical connection between the connectors 12, 22 is to use a flexible printed circuit board (PCB) similar to the type used in ink jet cartridge connectors. The reverse side of this flexible PCB has traces which are pulled out and connected to the appropriate cabling. Optionally, a chip with non-volatile memory may also be mounted on the flexible PCB. A suitable mating connector for this interface is a "pogo pin" type interface with pins mounted in a block (not shown), as commonly used in electronic testing apparatus.

Optionally, the actuator assembly in any of the embodiments described above may incorporate other actuatable features in addition to the basic articulation controls for manipulating the distal end of the insertion tube and transducer. For example, other mechanical connections besides the bending controls discussed above may be implemented, e.g., to transfer torque to the distal end of the probe. Controls for non-mechanical features may also be implemented on the handle, e.g., buttons for freezing the image, adjusting gain control or other functions. Optionally, the mechanical and electrical connections may be configured to be water-tight.

In all the above-described embodiments, when the transducer assembly is connected to the actuator assembly via the connector or connectors, the combination of the transducer assembly with the actuator assembly emulates both the electrical and mechanical operation of a conventional ultrasound probe. However, with the embodiments described above in connection with FIGS. 2-12, the doctor gains the ability to disconnect the actuator assembly from the transducer assembly, and leave the relatively compact distal transducer assembly section in position in the patient's esophagus. When this is done, only the connector 70, 22 and a portion of the flexible shaft 62, 20 will remain attached to the patient's body, and the handle, the actuator, and the cable that links the handle to the ultrasound system are disconnected from the patient. Since the hardware that stays attached to the patient's is smaller and lighter, it becomes much easier to move the patient around and to attend to the patient's needs, and is much less cumbersome as compared to the FIG. 1 embodiment in which the handle 104 and cable 106 stay attached to the patient as long as the transducer remains in position in the patient's esophagus. Preferably, the transducer assembly is configured so that the portion of the transducer assembly that remains outside of the patient's body is compact and has a mass of 250 g or less and a length of 70 cm or less.

Reducing the amount of hardware that is attached to the patient's is particularly advantageous for long term transesophageal ultrasound imaging, e.g., in situations where the probe remains installed in the patient for hours or days at a time. These advantages become even more important if the patient is awake or is not anesthetized, in which patient comfort becomes an even more important factor.

Advantages of the above-described embodiments include the fact that the device can be placed and left in-situ without causing problems with excessive bulk or cabling. In addition, by making the handle/actuator assembly separable from the transducer assembly, the transducer assembly may be made disposable and the handle may be made durable and reusable. This allows a less expensive disposable than would be possible if the entire probe were made disposable. It also allows the handle to be made to a higher standard than possible if the handle was also disposable, which may improve the tactile feedback to the user and ease of use.

While the above-described embodiments are discussed in the context of transesophageal echocardiography, similar probes may be used to obtain other transesophageal images as well as to obtain ultrasound images in cavities other than the esophagus. The connectorized construction may also be incorporated into probes, endoscopes, or catheters in non-ultrasound medical applications, and may even be used in non-medical uses where it is desirable to disconnect a proximal section while leaving the distal section in place. Numerous other modifications to the above-described embodiments will be apparent to persons skilled in the relevant arts, and are also included within the purview of the invention.

We claim:

1. A connectorized ultrasound probe comprising:
a compact first section having a distal end that is configured for insertion into a patient's body, with an ultrasound transducer located in the distal end; and
a second section configured to provide an electrical interface between the first section and an ultrasound system,
wherein the first section is attachable and detachable from the second section using at least one set of connectors,
wherein the second section includes at least one user-operated actuator, and the first and second sections are configured so that, when the first section is attached to the second section, actuation of the user-operated actuator causes the first section to bend, and
wherein the first and second sections are configured so that, when the first section is attached to the second section, (a) the ultrasound system can drive the ultrasound transducer by sending drive signals into the first section via the second section and (b) the ultrasound transducer in the first section can send return signals to the ultrasound system via the second section, wherein the transducer is transversely oriented with respect to a proximal-distal direction axis of the first section, wherein the first section is configured so that when the first section is inserted into the patient's esophagus with the ultrasound transducer positioned in the patient's stomach fundus, the portion of the first section that remains outside of the patient's body has a length of 70 cm or less and a mass of 250 g or less, and wherein the first section is sealed to prevent the entry of liquids.

2. A connectorized ultrasound probe configured for interfacing with an ultrasound system, the connectorized ultrasound probe comprising:

an actuator assembly including
 a user-operated actuator,
 a first connector including a first electrical interface and an output actuator, wherein the output actuator is operatively linked to the user-operated actuator so that an actuation of the user-operated actuator drives the output actuator, and
 a system interface that is configured to interface with the ultrasound system, wherein the system interface is operatively connected to the first electrical interface, and a transducer assembly having a proximal end and a distal end, wherein the transducer assembly includes
 an ultrasound transducer disposed in the distal end,
 a second connector located at the proximal end and configured to operatively mate with the first connector, the second connector having (a) a second electrical interface configured to operatively mate with the first electrical interface when the second connector is mated with the first connector and (b) a control actuator configured to operatively interact with the output actuator when the second connector is mated with the first connector so that the control actuator is actuated by the output actuator, wherein the second connector and the first connector are configured to permit easy mating of the second connector to the first connector and to permit easy removal of the second connector from the first connector,
 a flexible shaft positioned distally with respect to the second connector and proximally with respect to the distal end, the flexible shaft having a bending section,
 a circuit that operatively connects the second electrical interface with the ultrasound transducer,
 a bending mechanism that, in response to an actuation of the control actuator, causes the bending section to bend, wherein the actuator assembly and the transducer assembly are configured so that when the second connector is mated with the first connector, transducer driving signals applied to the system interface are routed to the ultrasound transducer via the first electrical interface and the second electrical interface, and return signals from the ultrasound transducer are routed to the system interface via the second electrical interface and the first electrical interface, wherein the actuator assembly and the transducer assembly are configured so that when the second connector is mated with the first connector, actuation of the user-operated actuator drives the output actuator, whereby the output actuator actuates the control actuator, which makes the bending mechanism cause the bending section to bend, and wherein the second connector has a mating face that faces in a direction that is roughly substantially perpendicular to a proximal-distal axis of the transducer assembly.

3. A transducer assembly configured for interfacing with an ultrasound system and an actuator assembly, the actuator assembly having a user-operated actuator and a first connector including (a) a first electrical interface and (b) an output actuator that is operatively linked to the user-operated actuator so that an actuation of the user-operated actuator drives the output actuator, wherein the transducer assembly comprises:

an ultrasound transducer disposed in a distal end of the transducer assembly;
a second connector located at a proximal end of the transducer assembly and configured to operatively mate with the first connector, the second connector having (a) a second electrical interface configured to operatively mate with the first electrical interface when the second connector is mated with the first connector and (b) a control actuator configured to operatively interact with the output actuator when the second connector is mated with the first connector so that the control actuator is actuated by the output actuator, wherein the second connector is configured to permit easy mating to the first connector and easy removal from the first connector;
a flexible shaft positioned distally with respect to the second connector and proximally with respect to the distal end, the flexible shaft having a bending section;
a circuit that operatively connects the second electrical interface with the ultrasound transducer; and
a bending mechanism that, in response to an actuation of the control actuator, causes the bending section to bend,
wherein the transducer assembly is configured so that when the second connector is mated with the first connector, transducer driving signals imposed on the first electrical interface are routed to the ultrasound transducer via the second electrical interface, and return signals from the ultrasound transducer are routed to the first electrical interface via the second electrical interface,
wherein the transducer assembly is configured so that the control actuator can be driven by the output actuator when the second connector is mated with the first connector, and
wherein the second connector has a mating face that faces sideways with respect to a proximal-to-distal direction along the transducer assembly.

4. The transducer assembly of claim 3, wherein the transducer assembly is dimensioned for performing transesophageal echocardiography and the transducer is transversely oriented with respect to a proximal-distal direction axis of the transducer assembly.

5. The transducer assembly of claim 3, wherein the transducer assembly is dimensioned for performing transesophageal echocardiography and the transducer comprises a two-dimensional array of elements.

6. The transducer assembly of claim 3, wherein the flexible shaft has a diameter of less than 6 mm.

7. The transducer assembly of claim 3, wherein the second connector is sealed to prevent liquids from entering.

8. The transducer assembly of claim 3, wherein the control actuator comprises a rotating member and the output actuator comprises another rotating member that engages the control actuator when the second connector is mated with the first connector.

9. The transducer assembly of claim 3, wherein the control actuator comprises a rotating pad and the output actuator comprises another rotating pad that engages the control actuator when the second connector is mated with the first connector.

10. The transducer assembly of claim 9, wherein the control actuator drives at least one pull wire, and wherein the at least one pull wire operates the bending mechanism.

11. The transducer assembly of claim 3, wherein the second connector snaps onto the first connector and can be snapped off from the first connector.

12. The transducer assembly of claim 3, further comprising a non-volatile memory device for storing data relating to the transducer assembly.

13. The transducer assembly of claim 3, wherein the transducer assembly is dimensioned so that when the transducer assembly is inserted into the patient's esophagus with the ultrasound transducer positioned in the patient's stomach fundus, the portion of the transducer assembly that remains outside of the patient's body is non-cumbersome for long term use.

14. The transducer assembly of claim 3, wherein the transducer assembly is dimensioned so that when the transducer assembly is inserted into the patient's esophagus with the ultrasound transducer positioned in the patient's stomach fundus, the portion of the transducer assembly that remains outside of the patient's body has a mass of 250 g or less.

15. The transducer assembly of claim 3, wherein the transducer assembly is dimensioned so that when the transducer assembly is inserted into the patient's esophagus with the ultrasound transducer positioned in the patient's stomach fundus, the portion of the transducer assembly that remains outside of the patient's body has a length of 70 cm or less.

16. The transducer assembly of claim 3,
wherein the transducer is transversely oriented with respect to a proximal-distal direction axis of the transducer assembly,
wherein the flexible shaft has a diameter of less than 6 mm,
wherein the transducer assembly is dimensioned so that when the transducer assembly is inserted into the patient's esophagus with the ultrasound transducer positioned in the patient's stomach fundus, the portion of the transducer assembly that remains outside of the patient's body has a mass of 250 g or less and a length of 70 cm or less, and
wherein the transducer assembly is sealed to prevent the entry of liquids.

17. The transducer assembly of claim 16, wherein the second connector has a mating face that faces sideways with respect to a proximal-to-distal direction along the transducer assembly.

18. An ultrasound probe comprising:
a first section having a distal end that is configured for insertion into a patient's body, with an ultrasound transducer located in the distal end and a first connector located at a proximal end of the first section, the first connector having a mating face that faces sideways with respect to a proximal-to-distal direction along the probe; and
a second section configured to provide an electrical interface between the first section and an ultrasound system, with a second connector located at a distal end of the second section, the second connector having a mating face that faces sideways with respect to a proximal-to-distal direction along the probe,
wherein the first section is attachable and detachable from the second section using the first and second connectors,
wherein the second section includes at least one user-operated actuator, and the first and second sections are configured so that, when the first section is attached to the second section, actuation of the user-operated actuator causes the first section to bend, and
wherein the first and second sections are configured so that, when the first section is attached to the second section, (a) the ultrasound system can drive the ultrasound transducer by sending drive signals into the first section via the second section and (b) the ultrasound transducer in the first section can send return signals to the ultrasound system via the second section.

19. The ultrasound probe of claim 18, wherein the first section is dimensioned for performing transesophageal echocardiography and the transducer is transversely oriented with respect to a proximal-distal direction axis of the first section.

20. The ultrasound probe of claim 18, wherein the first section is dimensioned for performing transesophageal echocardiography and the transducer comprises a two-dimensional array of elements.

21. The ultrasound probe of claim 18, wherein the first section is configured so that when the first section is inserted into the patient's esophagus with the ultrasound transducer positioned in the patient's stomach fundus, the portion of the first section that remains outside of the patient's body is non-cumbersome for long term use.

22. The ultrasound probe of claim 18, wherein the first section is configured so that when the first section is inserted into the patient's esophagus with the ultrasound transducer positioned in the patient's stomach fundus, the portion of the first section that remains outside of the patient's body has a mass of 250 g or less.

23. The ultrasound probe of claim 18, wherein the first section is configured so that when the first section is inserted into the patient's esophagus with the ultrasound transducer positioned in the patient's stomach fundus, the portion of the first section that remains outside of the patient's body has a length of 70 cm or less.

24. The ultrasound probe of claim 18, wherein the transducer is transversely oriented with respect to a proximal-distal direction axis of the first section, wherein the first section is configured so that when the first section is inserted into the patient's esophagus with the ultrasound transducer positioned in the patient's stomach fundus, the portion of the first section that remains outside of the patient's body has a length of 70 cm or less and a mass of 250 g or less, and wherein the first section is sealed to prevent the entry of liquids.

* * * * *

UNITED STATES PATENT AND TRADEMARK OFFICE
CERTIFICATE OF CORRECTION

| | | |
|---|---|---|
| PATENT NO. | : 8,070,685 B2 | Page 1 of 1 |
| APPLICATION NO. | : 11/279510 | |
| DATED | : December 6, 2011 | |
| INVENTOR(S) | : Edward Paul Harhen | |

It is certified that error appears in the above-identified patent and that said Letters Patent is hereby corrected as shown below:

Column 10,
lines 2-3 (claim 2), change "in a direction that is roughly substantially perpendicular to a proximal-distal axis of" to --sideways with respect to a proximal-to-distal direction along--

Signed and Sealed this
Thirty-first Day of January, 2012

David J. Kappos
*Director of the United States Patent and Trademark Office*